United States Patent [19]

Yamamuro et al.

[11] Patent Number: 4,554,246

[45] Date of Patent: Nov. 19, 1985

[54] PHOTOGRAPHIC SILVER HALIDE LIGHT-SENSITIVE MATERIAL

[75] Inventors: Kiyohiko Yamamuro; Yasuo Iwasa; Isamu Itoh, all of Kanagawa, Japan

[73] Assignee: Fuji Photo Film Co., Ltd., Kanagawa, Japan

[21] Appl. No.: 541,649

[22] Filed: Oct. 13, 1983

[30] Foreign Application Priority Data

Oct. 13, 1982 [JP]  Japan ................................ 57-179378
Dec. 29, 1982 [JP]  Japan ................................ 57-230912

[51] Int. Cl.$^4$ .......................... G03C 1/06; G03C 7/26; G03C 1/84
[52] U.S. Cl. ..................... 430/611; 430/551; 430/614; 430/955; 430/510
[58] Field of Search ............... 430/600, 603, 544, 611, 430/564, 613, 955, 614, 960, 445, 446, 507, 510, 551

[56] References Cited

U.S. PATENT DOCUMENTS

| | | | |
|---|---|---|---|
| 3,295,976 | 1/1967 | Abbott et al. | 430/377 |
| 3,397,987 | 8/1968 | Luckey et al. | 430/611 |
| 3,708,303 | 1/1973 | Salesin | 430/949 |
| 3,945,829 | 3/1976 | Zorn et al. | 430/507 |
| 4,458,011 | 7/1984 | Van de Sande et al. | 430/543 |

*Primary Examiner*—Mary F. Downey
*Attorney, Agent, or Firm*—Sughrue, Mion, Zinn, Macpeak, and Seas

[57] ABSTRACT

A photographic silver halide light-sensitive material is described. The material includes at least one of the compounds represented by general formula (I) as described below, their salts, and their precursors releasing the compounds of general formula (I) on cleavage under alkali conditions.

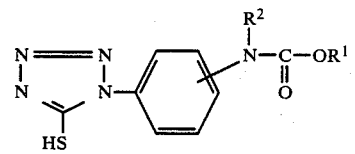

(the symbols are as defined in the appended claims). This light-sensitive material is less subject to a variation in photographic performance during the storage, in particular, the formation of fog is prevented.

11 Claims, No Drawings

PHOTOGRAPHIC SILVER HALIDE LIGHT-SENSITIVE MATERIAL

FIELD OF THE INVENTION

The present invention relates to a photographic silver halide light-sensitive material and, more particularly, to a photographic silver halide light-sensitive material whose photographic performance is prevented from varying during storage thereof. Moreover, it is concerned with a photographic silver halide light-sensitive material in which the formation of fog is inhibited without causing a reduction in sensitivity due to the control of development.

BACKGROUND OF THE INVENTION

The photographic performance (e.g., sensitivity and gradation and, in particular, fog) of a photographic silver halide light-sensitive material (hereinafter sometimes referred to merely as a "light-sensitive material") is liable to vary during the storage or when the light-sensitive material is stored for long periods of time. This variation in photographic performance with a lapse of time cannot be completely removed, but is desirable to be minimized. For this purpose, a number of investigations have heretofore been made.

It is known that to prevent the variation of photographic performance occurring during the storage of the light-sensitive material or the development thereof, heterocyclic compounds such as 1-phenyl-5-mercaptotetrazoles (as described in, e.g., Belgian Pat. No. 671,402, U.S. Pat. Nos. 3,295,976, 3,376,310, 3,615,616, 3,071,465, 3,420,664, 2,403,927, and Japanese Patent Application (OPI) No. 37436/75 (the term "OPI" as used herein refers to a "published unexamined Japanese patent application")), benzotriazoles (as described in, e.g., British Pat. Nos. 919,061, 768,438, U.S. Pat. Nos. 3,157,509, 3,082,088, and German Pat. No. 617,712), benzimidazoles (as described in, e.g., U.S. Pat. Nos. 3,317,578, 3,148,066, 3,511,663, British Pat. Nos. 271,475, 1,344,548, and German Pat. Nos. 708,424, 635,769, 2,205,539), and indazoles (as described in, e.g., U.S. Pat. Nos. 3,106,467, 3,420,670, 1,763,990 and 2,271,229) are added to light-sensitive materials or processing solutions. These compounds, however, have disadvantages in that their ability to inhibit the increase of fog during the storage is poor and they cause a reduction in sensitivity.

In color photographic light-sensitive materials, particularly those color photographic light-sensitive materials for cameras, the amount of silver salts as used therein is large and, furthermore, colloidal silver is used in a yellow filter layer and an antihalation layer. For this reason, the time required for the bleaching process is lengthened, and this constitutes a serious obstacle to the increase of the processing speed. 1-(Amidophenyl)-5-mercaptotetrazole, for example, is known as a compound having a high fog-inhibiting ability among the known antifoggants. This compound, however, suffers from the disadvantage that the processing speed is further decreased, since it readily forms a stable salt with silver and retards desilvering at the bleaching stage. This tendency is noticeable particularly when bleaching agents having a low bleaching force, such as persulfates, are used.

Hence, it is desired to obtain stabilizers which are capable of preventing the variation in photographic performance during the storage without retarding desilvering. However, none of the known compounds meets the foregoing requirement.

SUMMARY OF THE INVENTION

An object of the invention is to provide a light-sensitive material in which the variation of photographic performance, in particular, the formation of fog during storage is prevented.

Another object of the invention is to provide a light-sensitive material containing compounds which are capable of preventing the formation of fog without causing a reduction of sensitivity due to the control of development, permitting a substantial increase of sensitivity.

Still another object of the invention is to provide a color light-sensitive material in which the formation of fog is prevented by addition of compounds which do not retard desilvering at the bleaching stage.

A further object of the invention is to provide a color light-sensitive material in which desilvering is completed rapidly when bleaching agents having a low bleaching force, in particular, persulfates, are used, and the formation of fog is prevented.

It has been found that the above-described objects can be attained by adding the compounds represented by general formula (I) as described hereinafter or their salts, or their precursors undergoing cleavage under alkali conditions, releasing the compounds.

The present invention relates to a photographic silver halide light-sensitive material containing at least one of the compounds represented by general formula (I) as described hereinafter, their salts, and their precursors undergoing cleavage under alkali conditions, releasing the compounds:

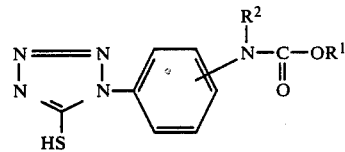

wherein $R^1$ is a substituted or unsubstituted aliphatic group, or a substituted or unsubstituted aromatic group, and $R^2$ is a hydrogen atom, a substituted or unsubstituted aliphatic group, or a substituted or unsubstituted aromatic group; $R^1$ and $R^2$ may be the same or different and may combine together to form a ring.

In general, compounds capable of forming more stable insoluble silver salts have a greater fog-preventing ability. In contrast, however, they tend to retard desilvering. It could not be expected and is astonishing that the compounds of the invention have a great fog-preventing ability and, moreover, have superior desilvering properties.

DETAILED DESCRIPTION OF THE INVENTION

The compounds of the invention will hereinafter be described in greater detail.

The aliphatic group for $R^1$ and $R^2$ of general formula (I) is preferably an alkyl group or an alkenyl group, containing up to 18 carbon atoms. Examples are a methyl group, an ethyl group, an n-propyl group, an n-butyl group, a tert-butyl group, an n-pentyl group, an n-hexyl group, a cyclohexyl group, an n-octyl group, an n-dodecyl group, an n-octadecyl group, and an allyl group.

The aromatic group for $R^1$ and $R^2$ is preferably an aryl group containing from 6 to 20 carbon atoms. Examples are a phenyl group and a naphthyl group.

Substituents for the aliphatic and aromatic groups of $R^1$ and $R^2$ include an alkoxyl group (e.g., a methoxy group and an ethoxy group), a halogen atom (e.g., a chlorine atom and a bromine atom), an alkyl group (e.g., a methyl group and an ethyl group), a phenyl group, an alkoxycarbonyl group (e.g., an ethoxycarbonyl group), an acyl group (e.g., an acetyl group), an acyloxyl group (e.g., an acetyloxy group), a cyano group, a nitro group, an alkylthio group (e.g., a methylthio group), a carbonamido group (e.g., an acetamido group), and a sulfonamido group (e.g., a methanesulfonamido group).

$R^1$ preferably contains from 1 to 8 carbon atoms and is an alkyl group or a phenyl group. Particularly preferred are a methyl group, an ethyl group, a propyl group, and a butyl group which may all be substituted or not substituted.

$R^2$ is preferably a hydrogen atom, or an alkyl group or a phenyl group, containing from 1 to 6 carbon atoms. Particularly preferred are a hydrogen atom, a methyl group, and an ethyl group.

Salts of the compounds represented by general formula (I) which can be used include alkali metal salts ($Li^+$, $Na^+$, and $K^+$), alkaline earth metal salts ($Mg^{2+}$ and $Ca^{2+}$), heavy metal salts ($Al^{3+}$, $Ni^{2+}$, $Zn^{2+}$, $Cu^{2+}$, $Co^{2+}$ and $Ag^+$), quaternary ammonium salts with, e.g., $NH_4^+$, $(CH_3)_4N^+$, $(C_4H_9)_4N^+$, $n\text{-}C_{12}H_{25}N^+(CH_3)_3$ and $n\text{-}C_{16}H_{33}N^+(CH_3)_3$, and quaternary phosphonium salts with e.g., $(C_4H_9)_4P^+$ and $C_6H_5CH_2P^+(CH_3)_3$.

As is well known, photographic additives having a group —SH can be used also as alkali cleavage type precursors. Hence, compounds resulting from replacement of H of the group —SH contained in the compounds of general formula (I) by groups capable of undergoing cleavage under alkali conditions can be used as precursors. Groups which undergo cleavage under alkali conditions include reverse-Michael type groups as described in, e.g., U.S. Pat. Nos. 3,888,677, 4,009,029 and 4,307,175, quinonemethide type groups as described in, e.g., U.S. Pat. Nos. 3,674,478, 3,932,480, 3,993,661, Japanese Patent Application (OPI) Nos. 135944/82, 135945/82, 136640/82 and U.S. Pat. No. 4,350,754, and ring cleavage type groups as described in, e.g., U.S. Pat. Nos. 4,310,612, 4,350,752 and 4,335,200. The present invention is not intended to be limited to the above-described compounds. All compounds capable of materially releasing the compounds of general formula (I) at the developing stage are included in the scope of the present invention.

Typical examples of the compounds represented by general formula (I) are shown below.

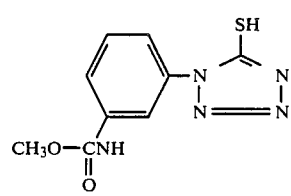

(1)

-continued

(2)

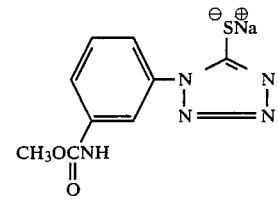

(3)

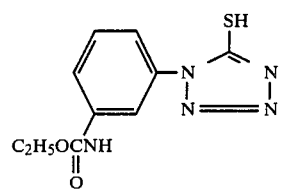

(4)

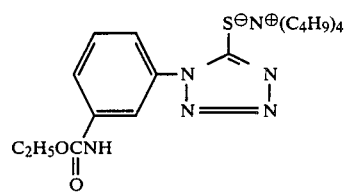

(5)

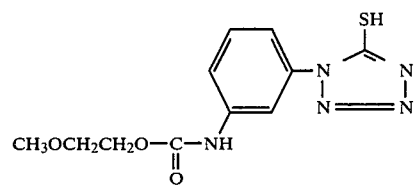

(6)

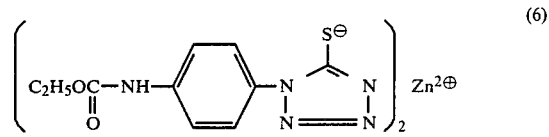

(7)

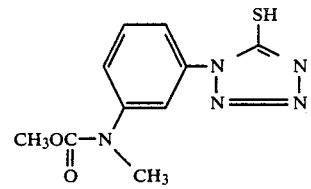

(8)

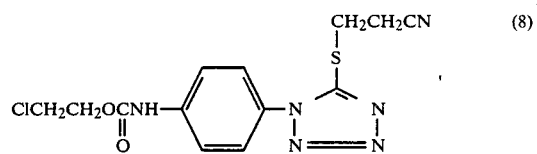

(9)

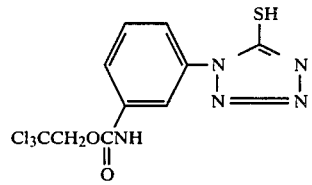

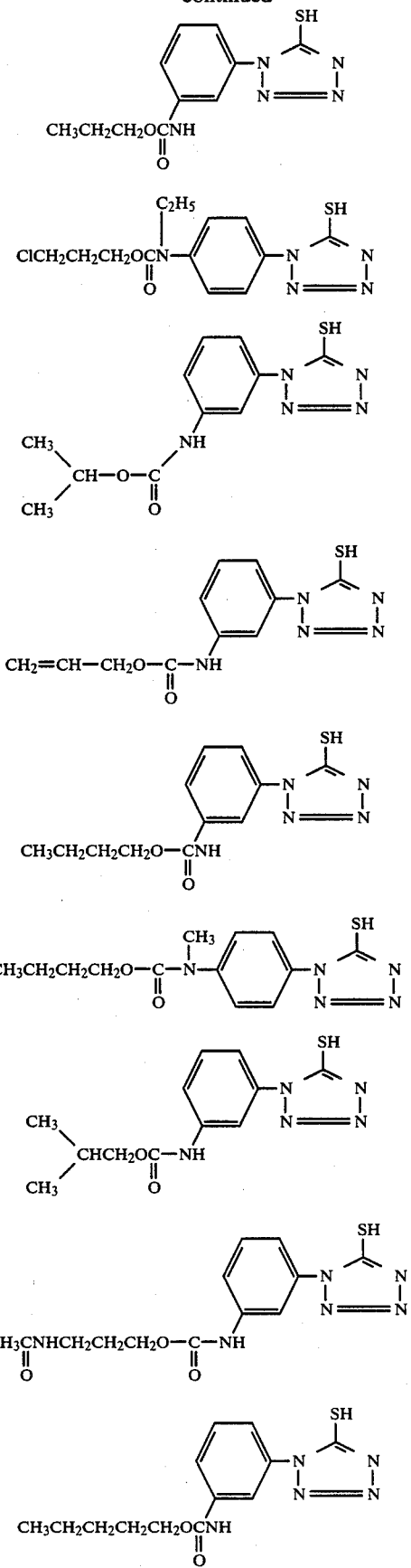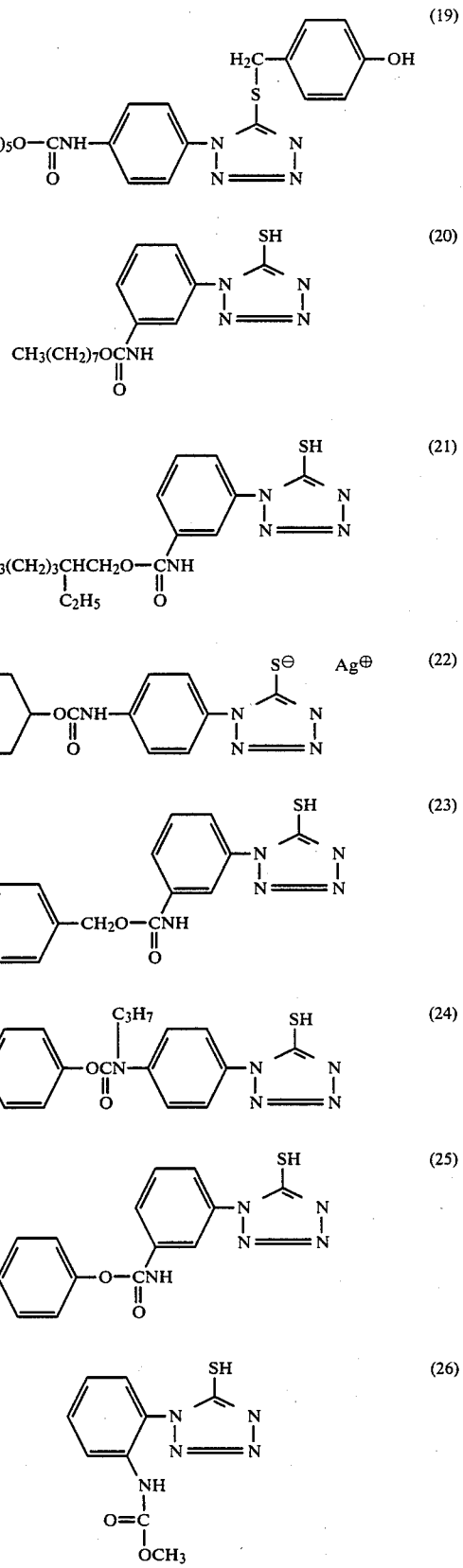

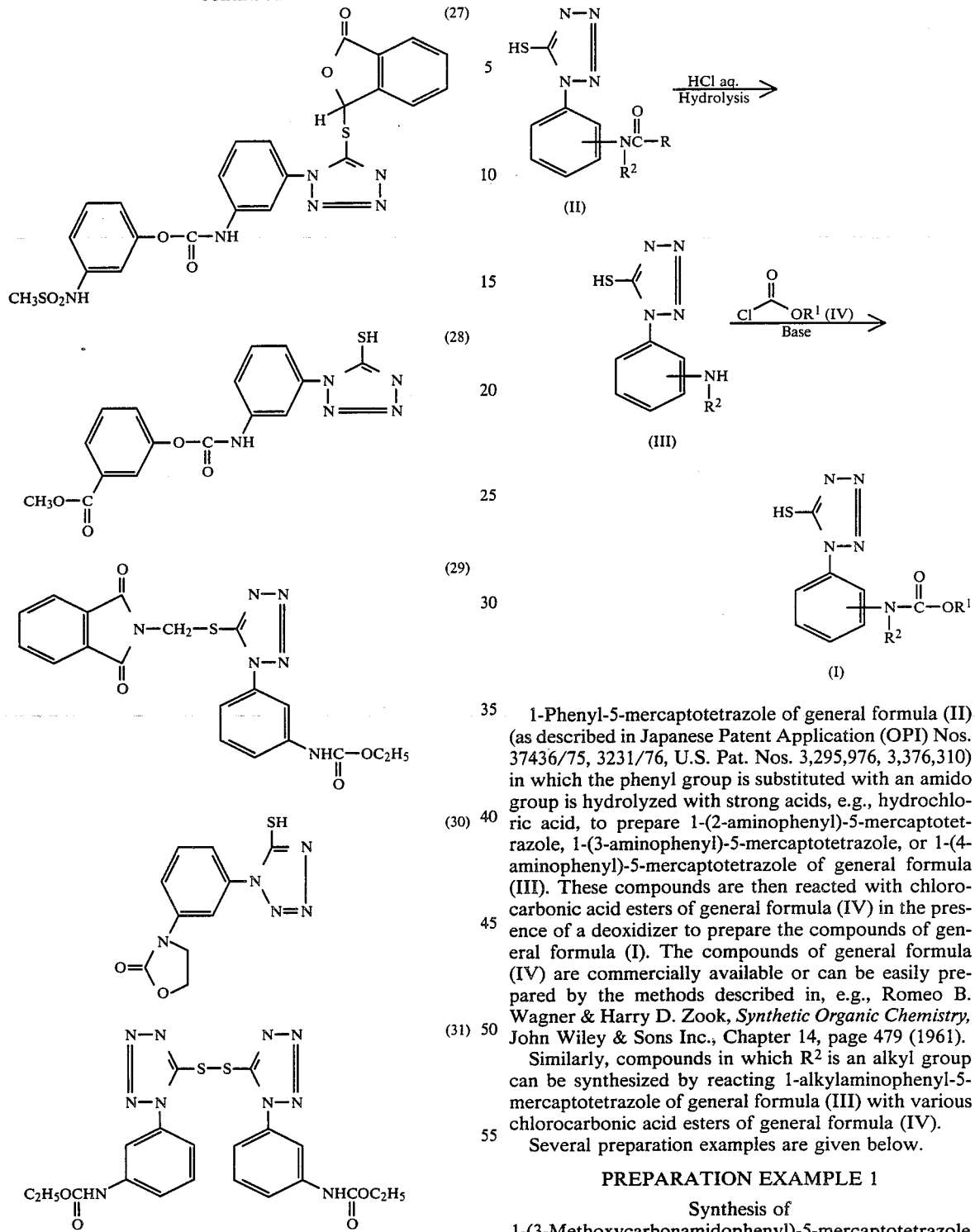

1-Phenyl-5-mercaptotetrazole of general formula (II) (as described in Japanese Patent Application (OPI) Nos. 37436/75, 3231/76, U.S. Pat. Nos. 3,295,976, 3,376,310) in which the phenyl group is substituted with an amido group is hydrolyzed with strong acids, e.g., hydrochloric acid, to prepare 1-(2-aminophenyl)-5-mercaptotetrazole, 1-(3-aminophenyl)-5-mercaptotetrazole, or 1-(4-aminophenyl)-5-mercaptotetrazole of general formula (III). These compounds are then reacted with chlorocarbonic acid esters of general formula (IV) in the presence of a deoxidizer to prepare the compounds of general formula (I). The compounds of general formula (IV) are commercially available or can be easily prepared by the methods described in, e.g., Romeo B. Wagner & Harry D. Zook, *Synthetic Organic Chemistry*, John Wiley & Sons Inc., Chapter 14, page 479 (1961).

Similarly, compounds in which $R^2$ is an alkyl group can be synthesized by reacting 1-alkylaminophenyl-5-mercaptotetrazole of general formula (III) with various chlorocarbonic acid esters of general formula (IV).

Several preparation examples are given below.

PREPARATION EXAMPLE 1

Synthesis of 1-(3-Methoxycarbonamidophenyl)-5-mercaptotetrazole (1)

1-(3-Acetamidophenyl)-5-mercaptotetrazole (0.51 mol) (120 g) was dispersed in 450 ml of ethanol. While stirring the dispersion at room temperature, 300 ml of concentrated hydrochloric acid was added. They were further reacted at room temperature for 3 hours. At the end of the time, the reaction mixture was cooled with ice. Crystals thus precipitated were collected and washed with acetone to obtain 110 g of 1-(3-aminophenyl)-5-mercaptotetrazole hydrochloride. This amine hydrochloride was dispersed in 750 ml of acetonitrile, and 123 ml of triethylamine was added thereto. Then, 41.5 g of methyl chlorocarbonate was further added thereto at room temperature.

They were further reacted at room temperature for 6 hours. At the end of the time, 2,200 ml. of water was added to the reaction mixture, and crystals precipitated were collected by filtration. These crystals were recrystallized from acetonitrile to obtain 68.7 g of the desired product (yield: 62%), m.p.: 198°–199° C.

In the same manner as above, compounds in which $R^1$ is an aliphatic group and which is substituted at the 3-position can be synthesized. Some of the compounds are shown below together with their melting points.

(2) 1-(3-Methoxycarbonamidophenyl)-5-mercaptotetrazole sodium salt, m.p. ~220° C. (decomposition)
(3) 1-(3-Ethoxycarbonamidophenyl)-5-mercaptotetrazole m.p. 185°–188° C.
(4) 1-(3-Ethoxycarbonamidophenyl)-5-mercaptotetrazole tetrabutylammonium salt, m.p. ~220° C. (decomposition)
(5) 1-[3-(2-Methoxyethoxycarbonamido)phenyl]-5-mercaptotetrazole, m.p. 155°–156° C.
(7) 1-(3-Methoxy-N-methylcarbonamidophenyl)-5-mercaptotetrazole, m.p. 145°–148° C.
(9) 1-[3-(2,2,2-trichloroethoxycarbonamido)phenyl]-5-mercaptotetrazole, m.p. 161°–163° C.
(10) 1-(3-Propoxycarbonamidophenyl)-5-mercaptotetrazole, m.p. 169°–170° C.
(12) 1-(3-Isopropoxycarbonamidophenyl)-5-mercaptotetrazole, m.p. 152°–154° C.
(13) 1-(3-Allyloxycarbonamidophenyl)-5-mercaptotetrazole, m.p. 157°–159° C.
(14) 1-(3-Butoxycarbonamidophenyl)-5-mercaptotetrazole, m.p. 150°–152° C.
(16) 1-[3-(2-Methylpropoxycarbonamido)phenyl]-5-mercaptotetrazole, m.p. 142°–144° C.
(17) 1-[3-(2-Acetamidopropoxycarbonamido)phenyl]-5-mercaptotetrazole, m.p. 169°–172° C.
(18) 1-(3-Pentyloxycarbonamidophenyl)-5-mercaptotetrazole, m.p. 168°–169° C.
(20) 1-(3-Octyloxycarbonamidophenyl)-5-mercaptotetrazole, m.p. 162°–164° C.
(21) 1-[3-(2-Ethylhexyloxycarbonamido)phenyl]-5-mercaptotetrazole, m.p. 157°–158° C.
(23) 1-(3-Benzyloxycarbonamido)-5-mercaptotetrazole, m.p. 153°–155° C.

PREPARATION EXAMPLE 2

Synthesis of 1-(3-Phenoxycarbonamidophenyl)-5-mercaptotetrazole (25)

1-(3-Aminophenyl)-5-mercaptotetrazole hydrochloride (24.9 g) was dispersed in 220 ml of acetonitrile, and 28 ml of triethylamine was added thereto. Then, 15.6 g of phenyl chlorocarbonate was added dropwise thereto at room temperature.

They were further reacted at room temperature for 6 hours. At the end of the time, 2,200 ml of water was added thereto, and crystals precipitated were collected by filtration. These crystals were recrystallized from acetonitrile to obtain 14.7 g of the desired product (yield: 46.9%), m.p. 190°–191° C.

2- and 4-substituted products can also be prepared in the same manner as above using, respectively, 1-(2-aminophenyl)-5-mercaptotetrazole and 1-(4-aminophenyl)-5-mercaptotetrazole in nearly the same yield.

PREPARATION EXAMPLE 3

Synthesis of 1-(3-Ethoxycarbonamidophenyl)-5-(2-phthalimidomethylthio)tetrazole (29)

2-Bromomethylphthalimide (0.05 mol) (12 g) was dissolved in 50 ml of tetrahydrofuran, and 50 ml of a tetrahydrofuran (THF) solution of $NaOCH_3$ (0.05 mol) and 13.3 g of 1-(3-ethoxycarbonamidophenyl)-5-mercaptotetrazole (3) (0.05 mol) were added dropwise thereto at room temperature. After the dropwise addition was completed, the resultant mixture was heated at 50° C. for 2 hours, and the solvent was then distilled away to obtain a crude product. This crude product was washed with cold water and then recrystallized from a mixed solvent of ethyl acetate and n-hexane to obtain about 16 g of the desired product as described above (yield: 75%), m.p. 151°–153° C.

The compound of the invention is added to at least one of the layers constituting the light-sensitive material. The amount of the compound being added varies depending on, e.g., the type of the compound and the type of the layer to be added, and cannot be determined indiscriminately. It has been found that when the compound of the invention is added to a silver halide emulsion layer in an amount of from $10^{-8}$ to $10^{-2}$ mol per mol of silver halide, and also when the compound of the invention is added to a layer containing colloidal silver in an amount of from $10^{-4}$ to 1 mol per mol of silver, the variation in photographic performance, particularly, the formation of fog during the storage can be inhibited. Preferably the amount of the compound of the invention being added is from $10^{-6}$ to $10^{-3}$ mol per mol of silver halide and from $10^{-3}$ to $10^{-1}$ mol per mol of silver.

The compound of the invention can be added to any auxiliary layers, such as a protective layer, a subbing layer, an intermediate layer, a yellow filter layer, and an antihalation layer, which are commonly provided on a light-sensitive material, as well as to a silver halide emulsion layer. It is preferred for the compound of the invention to be added to a layer containing silver halide or colloidal silver. Addition of the compound of the invention to a colloidal silver-containing layer, such as a yellow filter layer and an antihalation layer, of a color photographic light-sensitive material makes it possible to control an increase with time of fog due to the colloidal silver in an adjacent layer (an increased fog produced by the action as a physical developing nucleus of the colloidal silver diffused into the adjacent layer) without causing a reduction in sensitivity and, moreover, without reducing the desilvering properties of the colloidal silver.

Any of silver bromide, silver iodobromide, silver iodochlorobromide, silver chlorobromide, and silver chloride can be employed as the silver halide to be used in the photographic layer of the light-sensitive material of the invention. The mean grain size of silver halide grains in the photographic emulsion is not critical in the invention, but is preferably $3\mu$ or less. The mean grain size as used herein is determined based on the projected areas with a grain diameter as the grain size for those grains which are spherical or nearly spherical, or with an edge length as the grain size for those grains which are cubic. The grain size distribution may be narrow or broad.

Silver halide grains in the photographic emulsion may have a regular crystal form, such as a cubic or octahedral crystal form, or an irregular crystal form, such as a spherical or plate-like form, or a composite crystal form thereof. In addition, they may be composed of grains having different crystal forms.

Silver halide grains may be made of an inner portion and a surface layer which are different in phase, or may be in a uniform phase. They may be those in which a latent image is formed mainly on the surface thereof, or those in which a latent image is formed mainly in the interior thereof.

The photographic emulsion as used herein can be prepared by the methods described in, e.g., P. Glafkides, *Chimie et Physique Photographique*, Paul Montel Co. (1967), G. F. Duffin, *Photographic Emulsion Chemistry*, The Focal Press Co. (1966), and V. L. Zelikman et al., *Making and Coating Photographic Emulsion*, The Focal Press Co. (1964). That is, any of an acid method, a neutral method, an ammonia method, and so forth can be employed. Soluble silver salts and soluble halides can be reacted by any of a single jet mixing method, a double jet mixing method, and a combination thereof.

In addition, a so-called reversal mixing method in which grains are formed in the presence of an excess of silver ions can be employed. As one embodiment of the double jet mixing method, a so-called controlled double jet method in which pAg in the liquid phase where silver halide is formed is maintained at a predetermined level can be employed.

These methods produce silver halide emulsions in which silver halide has a regular crystal form and its grain size is nearly uniform.

Two or more silver halide emulsions which are prepared separately may be used in combination with each other.

The formation of silver halide grains or their physical ripening may be performed in the presence of cadmium salts, zinc salts, lead salts, thallium salts, iridium salts or its complex salts, rhodium salts or its complex salts, iron salts or its complex salts, etc.

Both a negative type emulsion forming a surface latent image and a direct reversion type emulsion can be used in the invention. The emulsion of the latent type includes an inner latent image type emulsion and a direct reversion type emulsion which is fogged previously.

Inner latent image type silver halide emulsions which can be used advantageously in the invention include a conversion type emulsion, a core/shell type emulsion, an emulsion containing therein different metals, etc., as described in, for example, U.S. Pat. Nos. 2,592,250, 3,206,313, 3,447,927, 3,761,276 and 3,935,014.

Typical examples of nucleus-forming agents for emulsions of the type as described above are hydrazines described in U.S. Pat. Nos. 2,588,982 and 2,563,785, hydrazides and hydrazones described in U.S. Pat. No. 3,227,552, quaternary salt compounds described in British Pat. No. 1,283,835, Japanese Patent Publication No. 38164/74, U.S. Pat. Nos. 3,734,738, 3,719,494 and 3,615,615, sensitizing dyes containing a nucleating substituent having a fogging action in the dye molecule as described in U.S. Pat. No. 3,718,470, and acylhydrazinophenylthiourea compounds described in U.S. Pat. Nos. 4,030,925 and 4,031,127.

Silver halide emulsions are usually subjected to chemical sensitization although they can be used as primitive emulsions without application of chemical sensitization. This chemical sensitization can be performed by the methods described in the above-described references by P. Glafkides and V. L. Zelikman et al., and H. Frieser ed., *Die Grundlagen der Photographischen Prozesse mit Silberhalogeniden*, Akademische Verlagsgesellschaft (1968). That is, a sulfur sensitization method using compounds containing sulfur capable of reacting with silver ions or active gelatin, a reduction sensitizing method using reducing substances, a noble metal sensitization method using nobel metal (e.g., gold) compounds and so forth can be used singly or in combination with each other.

Sulfur sensitizers which can be used include thiosulfates, thioureas, thiazoles, and rhodanines. Typical examples of these compounds are described in U.S. Pat. Nos. 1,574,944, 2,410,689, 2,278,947, 2,728,668 and 3,656,955. Reduction sensitizers which can be used include stannous salts, amines, hydrazine derivatives, formamidinesulfinic acid, and silane compounds. Typical examples of these compounds are described in U.S. Pat. Nos. 2,487,850, 2,419,974, 2,518,698, 2,983,609, 2,983,610 and 2,694,637. For noble metal sensitization, as well as gold complex salts, complex salts of Group VIII metals (e.g., platinum, iridium and palladium) of the Periodic Table can be used. Typical examples are described in, for example, U.S. Pat. Nos. 2,399,083, 2,488,060, and British Pat. No. 618,061.

Photographic emulsions may be subjected to spectral sensitization using methine dyes, for example. Dyes which can be used for this spectral sensitization include cyanine dyes, merocyanine dyes, composite cyanine dyes, composite merocyanine dyes, holopolar cyanine dyes, hemicyanine dyes, styryl dyes, and hemioxonol dyes. Especially useful dyes are those belonging to the cyanine dyes, merocyanine dyes, and composite merocyanine dyes.

Useful sensitizing dyes are those described in, for example, German Pat. No. 929,080, U.S. Pat. Nos. 2,231,658, 2,493,748, 2,503,776, 2,519,001, 2,912,329, 3,655,394, 3,656,959, 3,672,897, 3,694,217, British Pat. No. 1,242,588, and Japanese Patent Publication No. 14030/69.

In addition to layers composed of light-sensitive silver halide emulsions as described above, those layers composed of substantially light-insensitive and finely grained silver halide emulsions may be provided for various purposes; for example, to increase granularity and sharpness. These substantially light-insensitive and finely grained silver halide emulsion layers can be provided on the top of the light-sensitive silver halide emulsion layer, or between the light-sensitive silver halide emulsion layer and the colloidal silver layer (e.g., a yellow filter layer and an antihalation layer).

For the purpose of increasing sensitivity or contrast, or accelerating development, polyalkylene oxides or their ether, ester, amine or like derivatives, thioether compounds, thiomorpholines, quaternary ammonium salt compounds, urethane derivatives, urea derivatives, imidazole derivatives, 3-pyrazolidones, etc., may be added to the light-sensitive material of the invention. For example, the compounds described in U.S. Pat. Nos. 2,400,532, 2,423,549, 2,716,062, 3,617,280, 3,772,021 and 3,808,003 can be used.

Gelatin is advantageous to use as a binder for the photographic emulsion layers and other layers. Other hydrophilic colloids can also be used. For example, gelatin derivatives, graft copolymers of gelatin and other polymers, proteins such as albumin and casein, cellulose derivatives such as hydroxyethyl cellulose, carboxymethyl cellulose, and cellulose sulfate, saccharide derivatives such as sodium alginate and starch derivatives, and a wide variety of synthetic hydrophilic polymer substances such as homo- and copolymers, e.g., polyvinyl alcohol, polyvinyl alcohol partial acetal, poly(N-vinyl) pyrrolidone, polyacrylic acid, polymethacrylic acid, polyacrylamide, polyvinyl imidazole, and polyvinyl pyrazole, can be used.

In addition to lime-treated gelatin, acid-treated gelatin and enzyme-treated gelatin as described in *Bull. Soc. Sci. Phot., Japan,* No. 16, page 30 (1966) may be used. In addition, hydrolyzates and enzyme decomposition products of gelatin can be used. As gelatin derivatives, those compounds as obtained by reacting gelatin with, for example, acid halides, acid anhydrides, isocyanates, bromoacetic acid, alkanesultones, vinylsulfonamides, maleinimide compounds, polyalkylene oxides, and epoxy compounds are used. Typical examples are described in, for example, U.S. Pat. Nos. 2,614,928, 3,132,945, 3,186,846, 3,312,553, British Pat. Nos. 861,414, 1,033,189, 1,005,784, and Japanese Patent Publication No. 26845/67.

As the gelatin graft copolymers as described above, those compounds resulting from graft polymerization of gelatin and homo- or copolymers of vinyl monomers such as acrylic acid and methacrylic acid, or their ester, amide and like derivatives, acrylonitrile, and styrene can be used. Especially preferred are those graft polymers resulting from graft polymerization of gelatin and polymers compatible with gelatin to a certain extent, such as polymers of acrylic acid, methacrylic acid, acrylamide, methacrylamide, and hydroxyalkyl methacrylate. Examples of such compounds are described in, for example, U.S. Pat. Nos. 2,763,625, 2,831,767 and 2,956,884.

Typical synthetic hydrophilic polymer substances are described in, for example, West German Patent Application (OLS) No. 2,312,708, U.S. Pat. Nos. 3,620,751, 3,879,205, and Japanese Patent Publication No. 7561/68.

The light-sensitive material of the invention can contain various compounds as antifoggants or stabilizers as well as the compounds represented by general formula (I); that is, a number of compounds known as antifoggants or stabilizers, for example, azoles such as benzothiazolium salts, nitroindazoles, triazoles, benzotriazoles, and benzimidazoles (particularly nitro- or halogen-substituted compounds); heterocyclic mercapto compounds such as mercaptothiazoles, mercaptobenzothiazoles, mercaptobenzimidazoles, mercaptothiadiazoles, mercaptotetrazoles (particularly 1-phenyl-5-mercaptotetrazole), and mercaptopyrimidines; the foregoing heterocyclic mercapto compounds containing water-soluble groups such as a carboxyl group and a sulfone group; thioketo compounds such as oxazolinethione; azaindenes such as tetraazaindenes (particularly 4-hydroxy-substituted (1,3,3a,7)tetraazaindenes); benzenethiosulfonic acids; and benzenesulfinic acids can be added to the light-sensitive material of the invention. The amounts of these antifoggants or stabilizers to be added are preferably less than $10^{-4}$ mol per mol of silver.

In connection with typical examples of such compounds and methods of using them, U.S. Pat. Nos. 3,954,474, 3,982,947, 4,021,248, and Japanese Patent Publication No. 28660/77 can be referred to.

Inorganic or organic hardeners may be introduced in the photographic emulsion layer and other layers of the light-sensitive material of the invention. For example, chromium salts (e.g., chromium alum and chromium acetate), aldehydes (e.g., formaldehyde, glyoxal, and glutaraldehyde), N-methylol compounds (e.g., dimethylolurea and methyloldimethylhydantoyl), dioxane derivatives (e.g., 2,3-dihydroxydioxane), active vinyl compounds (e.g., 1,3,5-triacryloylhexahydro-s-triazine and 1,3-vinylsulfonyl-2-propanol), active halogeno compounds (e.g., 2,4-dichloro-6-hydroxy-s-triazine), and mucohalogeno acids (e.g., mucochloric acid and mucophenoxychloric acid) can be used singly or in combination with each other.

Various surfactants may be introduced in the photographic emulsion layer and other layers of the light-sensitive material of the invention as coating aid or for various purposes, e.g., to prevent charging, improve sliding properties, accelerate dispersion and emulsification, prevent adhesion, or to improve photographic characteristics (e.g., acceleration of development, high contrast, and sensitization).

Surfactants which can be used are:

Nonionic surfactants such as saponin (steroid-based), alkylene oxide derivatives (e.g., polyethylene glycol, polyethylene glycol/polypropylene glycol condensates, polyethylene glycol alkyl ethers or glycol alkylaryl ethers, polyethylene glycol esters, polyethylene glycol sorbitan esters, polyalkylene glycol alkylamine or amides, and polyethylene oxide adducts of silicone), glycidol derivatives (e.g., alkenyl succinic acid polyglyceride and alkylphenol polyglyceride), fatty acid esters of polyhydric alcohols, and alkyl esters of saccharides;

Anionic surfactants containing acidic groups, e.g., a carboxyl group, a sulfo group, a phospho group, a sulfate group, and a phosphate group, for example, alkylcarboxylic acid salts, alkylsulfonic acid salts, alkylbenzenesulfonic acid salts, alkylnapthalenesulfonic acid alkyl sulfates, alkyl phosphates, N-acyl-N-alkyltauric acids, sulfosuccinic acid esters, sulfoalkylpolyoxyethylene alkylphenyl ethers, and polyoxyethylene alkyl phosphates;

Amphoteric surfactants such as aminoacids, aminoalkylsulfonic acids, aminoalkyl sulfates or phosphates, alkylbetaines, and aminooxides; and Cationic surfactants such as alkylamine salts, aliphatic or aromatic quaternary ammonium salts, heterocyclic quaternary ammonium salts, e.g., pyridinium and imidazolium, and aliphatic or heterocyclic ring-containing phosphonium or sulfonium salts.

The photographic emulsion layers of the light-sensitive material of the invention contain color-forming couplers, e.g., compounds capable of forming color by oxidative coupling with aromatic primary amine developers (e.g., phenylenediamine derivatives and aminophenol derivatives) at the color developing stage. They are magenta couplers such as a 5-pyrazolone coupler, a pyrazolobenzimidazole coupler, a cyanoacetylcumarone coupler, and an open-chain acylacetonitrile coupler; yellow couplers such as an acylacetamide coupler (e.g., benzoylacetanilides and pivaloylacetanilides); and cyan couplers such as a naphthol coupler and a phenol coupler. Non-diffusing couplers containing a hydrophobic group called a ballast group in the molecule thereof are desirable to use. These couplers may be 4-equivalent or 2-equivalent relative to silver ion. Colored couplers having the color correction effect, or so-called DIR couplers releasing a development inhibitor with development can be used. In addition to DIR couplers, colorless DIR coupling compounds producing a colorless coupling reaction product and releasing a development inhibitor, and DIR redox compounds can be used.

Suitable examples of the magenta couplers are described in, for example, U.S. Pat. Nos. 2,600,788, 2,983,608, 3,062,653, 3,127,269, 3,311,476, 3,419,391, 3,519,429, 3,558,319, 3,582,322, 3,615,506, 3,834,908, 3,891,445, West German Pat. No. 1,810,464, West German Patent Application (OLS) Nos. 2,408,665, 2,417,945, 2,418,959, 2,424,467, Japanese Patent Publication No. 6031/65, Japanese Patent Application (OPI) Nos. 20826/76, 13041/75, 58922/77, 129538/74, 74027/74, 159336/75, 42121/77, 74028/74, 60233/75, 26541/76, 55122/78 and 118034/80.

Suitable examples of the yellow couplers are described in, for example, U.S. Pat. Nos. 2,875,057, 3,265,506, 3,408,194, 3,551,155, 3,582,322, 3,725,072, 3,891,445, 3,894,875, 4,157,919, West German No. 1,547,868, West German Patent Application Laid-Open Nos. 2,219,917, 2,261,361, 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77, 115219/77 and 82332/78.

Suitable examples of the cyan couplers are described in, for example, U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411, 4,004,929, 4,124,396, West German Patent Application (OLS) Nos. 2,414,830, 2,454,329, Japanese Patent Application (OPI) Nos. 59838/73, 26034/76, 5055/73, 146828/76, 69624/77, 90932/77, 65134/81, 29235/81 and 99341/81.

As colored couplers, those couplers described in, for example, U.S. Pat. Nos. 3,476,560, 2,521,908, 3,034,892, Japanese Patent Publication Nos. 2016/69, 22335/63, 11304/67, 32461/69, Japanese Patent Application (OPI) Nos. 26034/76, 42121/77, and West German Patent Application (OLS) No. 2,418,959 can be used.

As DIR couplers, the o-aminoazo type DIR couplers described in U.S. Pat. No. 3,148,062, the thioether type DIR couplers described in U.S. Pat. No. 3,227,554, the 2-benzotriazolyl type DIR couplers described in U.S. Pat. No. 3,617,291, the 1-benzotriazolyl type DIR couplers described in, for example, West German Patent Application (OLS) No. 2,414,006, Japanese Patent Application (OPI) Nos. 82424/77 and 17627/77, the nitrogen-containing heterocyclic ring-substituted acetic acid ester type DIR couplers described in Japanese Patent Application (OPI) Nos. 30591/75 and 82423/77, the 2-equivalent type DIR cyan couplers described in West German Patent Application (OLS) No. 2,527,652, Japanese Patent Application (OPI) Nos. 90932/77 and 146828/76, the malonic acid diamide type DIR couplers described in Japanese Patent Application (OPI) No. 69624/77, the DIR couplers having a group to be released as controlled in the timing, described in U.S. Pat. No. 4,248,962 and Research Disclosure, No. 21228, etc., can be used.

Colorless DIR coupling compounds which can be used include the thioether type cyclic colorless DIR compounds described in, for example, British Pat. No. 1,423,588, West German Patent Application (OLS) Nos. 2,405,442, 2,523,705, 2,529,350, 2,448,063, and U.S. Pat. No. 3,938,996, the thioether type chain-like colorless DIR compounds described in U.S. Pat. Nos. 3,632,345 and 3,928,041, the benzotriazolyl type colorless DIR compounds described in Japanese Patent Application (OPI) Nos. 147716/75, 105819/76 and 67628/77, and the picolinium type DIR coupling compounds described in Japanese Patent Application (OPI) No. 72433/76.

DIR redox compounds which can be used include the DIR hydroquinones described in, for example, U.S. Pat. No. 3,639,417, West German Patent Application (OLS) No. 2,460,417, and U.S. Pat. No. 3,297,445, and the DIR redox type couplers described in Japanese Patent Application (OPI) No. 57828/77.

The photographic emulsions of the invention may contain dye image-forming compounds (e.g., dye developing agents, dye releasing redox compounds, and DIR couplers) as used in so-called diffusion transfer photography. Compounds which can be used are described in, for example, U.S. Pat. Nos. 4,053,312, 4,055,428, 4,076,529, 4,152,153, 4,135,929, Japanese Patent Application (OPI) Nos. 149328/78, 104343/76, 46730/78, 130122/79, 3819/78 and Japanese Patent Application (OPI) Nos. 12642/81, 16130/81, 16131/81.

The light-sensitive material of the invention can contain developing agents. Developing agents which can be used are described in Research Disclosure, Vol. 176, page 29 "Developing Agents".

In the light-sensitive material of the invention, dyes may be incorporated in the photographic emulsion layer and other layers as filter dyes or for various purposes of, e.g., prevention of irradiation. As such dyes, the compounds described in Research Disclosure, Vol. 176, pp. 25 to 26 "Absorbing and Filter Dyes".

The light-sensitive material of the invention may further contain antistatic agents, plasticizers, matting agents, lubricants, ultraviolet absorbing agents, fluorescent brightening agents, air fog-preventing agents, and the like.

The silver halide emulsion layers and/or other constitutive layers are coated on a support. Thic coating can be performed by the methods described in Research Disclosure, Vol. 176, pp. 27-28, "Coating Procedures".

Supports which can be used are described in Research Disclosure, Vol. 176, page 28, "Supports".

The light-sensitive material of the invention has various applications. For example, it can be used as a white and black negative film, a white and black paper film, a color positive film, a color paper film, a color negative film, a color reversal film (containing or not containing couplers), a print-making photographic light-sensitive material (e.g., a lith film), a light-sensitive material for use in cathode ray tube display), a light-sensitive material for X-ray recording (particularly a direct or indirect photographic material using a screen), a light-sensitive material for the colloid transfer process (described in, for example, U.S. Pat. No. 2,716,059), the silver salt diffusion transfer process (described in, for example, U.S. Pat. Nos. 2,352,014, 2,543,181, 3,020,155 and 2,861,885), the color diffusion transfer process (described in, for example, U.S. Pat. Nos. 3,087,817, 3,187,567, 2,983,606, 3,253,915, 3,227,550, 3,227,551, 3,227,552, 3,415,644, 3,415,645, 3,415,646, and Research Disclosure, Vol. 151, No. 15162, pp. 75-87 (November, 1976), the imbibition transfer process (described in, for example, U.S. Pat. No. 2,882,156), or the silver dye bleaching method (described in, for example, Friedman,

*History of Color Photography*, American Photographic Publishers Co., (1944) (particularly Chapter 24), and *British Journal of Photography*, Vol. 111, pp. 308–309 (Apr. 7, 1964), a direct positive light-sensitive material (described in, for example, U.S. Pat. Nos. 2,497,875, 2,588,982, 3,367,778, 3,501,306, 3,501,305, 3,672,900, 3,477,852, 2,717,833, 3,023,102, 3,050,395 and 3,501,307), a heat developing light-sensitive material (described in, for example, U.S. Pat. Nos. 3,152,904, 3,312,550, 3,148,122 and British Pat. No. 1,110,046), or a physical developing light-sensitive material (described in, for example, British Pat. Nos. 920,277 and 1,131,238).

The light-sensitive material of the invention can be used advantageously, in particular, as an inner type color light-sensitive material of the multilayer structure (particularly a reversal color light-sensitive material and a negative color light-sensitive material).

A layer structure which allows the light-sensitive material of the invention to exhibit its effects especially efficiently is such that a colloidal silver antihalation layer, an intermediate layer, a red-sensitive layer, an intermediate layer, a green-sensitive layer, a colloidal silver yellow filter layer, a blue-sensitive layer, and a protective layer are coated on a support in that order. The foregoing red-sensitive, green-sensitive and blue-sensitive layers may be each divided into low sensitivity and high sensitivity layers. In addition, a layer structure as described in Japanese Patent Publication No. 15495/74 in which at least one of red-sensitive, green-sensitive and blue-sensitive layers is divided into three partial layers, a layer structure as described in Japanese Patent Application (OPI) No. 49027/76 which comprises a high sensitivity emulsion layer unit and a low sensitivity emulsion layer unit, and a layer structure as described in West German Patent Application (OLS) Nos. 2,622,922, 2,622,923, 2,622,924, 2,704,826 and 2,704,797 can be employed.

The light-sensitive material of the invention is exposed imagewise to light in the usual manner to obtain a photographic image. For this exposure, any of the known light sources, e.g., a sunlight, a tungsten lamp, a fluorescent lamp, a mercury lamp, a xenon arc lamp, a carbon arc lamp, a xenon flash lamp, and a cathode ray tube flying spot, can be used. Exposure time may be, of course, within a range of from 1/1,000 to 1 second which is usually used for cameras. Exposure of shorter than 1/1,000 second, for example, exposure of from $1/10^4$ to $1/10^6$ second using a xenon flash lamp or a cathode ray tube, and exposure of longer than 1 second can be employed. If necessary, the spectral composition of light to be used for the exposure can be controlled by means of a color filter. Laser light can be used for the exposure. Furthermore, the light-sensitive material of the invention may be exposed to light generated by a fluorescent body which is excited by electron rays, X-rays, $\gamma$-rays, $\alpha$-rays, or the like.

Any known method can be employed for the photographic processing of the light-sensitive material of the invention,. The known processing solutions can be used. The processing temperature is normally chosen within the range of from 18° to 50° C., although it may be higher than 50° C. or lower than 18° C. A developing processing (black and white photographic processing) to form a silver image, or a color photographic processing including a developing step to form a dye image can be used depending on the purpose for which the light-sensitive material of the invention is used.

Developers for use in the black and white photographic processing can contain the known developing agents. Developing agents which can be used include dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds similar to the condensate of a 1,2,3,4-tetrahydroquinoline ring and an indolene ring as described in U.S. Pat. No. 4,067,872. These compounds can be used singly or in combination with each other. In general, the developers may contain other known additives such as preservatives, alkali agents, pH buffers, and antifoggants, and moreover, if desired, dissolving aids, color controllers, development accelerators, surfactants, defoaming agents, hard water softening agents, hardeners, tackifiers, and the like.

A so-called "lith" type of development can be applied to the photographic emulsions of the invention. This lith type of development means a developing procedure in which for photographic reproduction using line images or photographic reproduction using dots of half tone images, dihydroxybenzenes are usually used as a developing agent and the development is performed infectiously at a low sulfite ion concentration (the details are described in Mason, *Photographic Processing Chemistry*, pp. 163–165 (1966)).

As a special developing system, a method can be used in which a developing agent is incorporated in a light-sensitive material, for example, in an emulsion layer thereof and the light-sensitive material is processed in an aqueous alkali solution to effect development. Hydrophobic ones of the developing agents can be subjected to latex dispersion and added to the emulsion layer as described in *Research Disclosure*, No. 169 as RD-16928. This developing process may be applied in combination with a silver salt stabilization process using thiocyanates.

As fixing solutions, those having the compositions generally used can be employed. Fixing agents which can be used are organosulfur compounds known to have the effect as the fixing agent, as well as thiosulfates and thiocyanates. These fixing solutions may contain water-soluble aluminum salts as a hardener.

Dye images can be formed in the usual manner, such as by the negative positive method (described in, for example, *Journal of the Society of Motion Picture and Television Engineers*, Vol. 61, pp. 667–701 (1953)), the color reversal method in which a negative silver image is formed with a developer containing a black and white developing agent to form a negative silver image, the negative silver image thus formed is subjected at least once to uniform exposure or other suitable fogging treatment, and subsequently, color development is performed to obtain a dye positive image, and the silver dye bleaching method in which a photographic emulsion layer containing a dye is exposed to light and developed to form a silver image, and with the thus-formed silver image as a bleaching catalyst, the dye is bleached.

A color developer generally comprises an alkaline aqueous solution containing a color developing agent. As such color developing agents, the known primary aromatic amine developers, e.g., phenylenediamines such as 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$- methanesulfonamidoethylaniline, and 4-amino-3-methyl-N-ethyl-N-β-methoxyethylaniline, can be used.

In addition, the compounds described in, for example, L. F. A. Mason, *Photographic Processing Chemistry*, Focal Press Co., pp. 226-229 (1966), U.S. Pat. Nos. 2,193,015 and 2,592,364, and Japanese Patent Application (OPI) No. 64933/73 can be used.

These color developers can further contain pH buffers, such as sulfites, carbonates, borates and phosphates of alkali metals, development inhibitors or antifoggants, such as bromides, iodides and organic antifoggants, and the like. If necessary, they may contain hard water-softening agents, preservatives, e.g., hydroxylamine, organic solvents, e.g., benzyl alcohol and diethylene glycol, development accelerators, e.g., polyethylene glycol, quaternary ammonium salts and amines, dye-forming couplers, competitive couplers, foggants, e.g., sodium borohydride, auxiliary developing agents, e.g., 1-phenyl-3-pyrazolidone, tackifiers, polycarboxylic acid-based chelating agents as described in U.S. Pat. No. 4,083,723, antioxidants as described in West German Patent Application (OLS) No. 2,622,950, etc.

After color development, the photographic emulsion layer is usually bleached. This bleaching may be performed simultaneously with a fixing treatment or they may be performed separately. Bleaching agents which can be used include compounds of multivalent metals such as iron (III), cobalt (III), chromium (VI), and copper (II), peracids, quinones, and nitroso compounds. Typical examples are ferricyanides, perchlorates, organic complex salts of iron (III) or cobalt (III), complex salts of organic acids such as aminopolycarboxylic acids, e.g., ethylenediaminetetraacetic acid, nitrilotriacetic acid, and 1,3-diamino-2-propanoltetraacetic acid, citric acid, tartaric acid, and malic acid, persulfates, permanganates, and nitrosophenol.

The rate of desilvering is high even when the light-sensitive material of the invention is processed with, in particular, bleaching agents having a low bleaching force, such as persulfates. Hence, it is preferred to treat with such bleaching agents not causing pollution.

Bleaching or bleach-fixing solutions can contain bleach accelerators as described in, for example, U.S. Pat. Nos. 3,042,520, 3,241,966, Japanese Patent Publication Nos. 8506/70 and 8836/70, thiol compounds as described in Japanese Patent Application (OPI) No. 65732/78, and other various additives.

When bleaching agents having a low bleaching force, such as persulfates, are used, bleach accelerators may be added to the bleaching solution, the bleach-fixing solution or their pre-baths. As such bleach accelerators, the compounds described in, for example, U.S. Pat. Nos. 3,772,020, 3,893,858, 3,707,374, Japanese Patent Publication No. 28227/76, Japanese Patent Application (OPI) No. 26506/80, and *Research Disclosure*, No. 15704 can be used.

The present invention is described in greater detail with reference to the following Examples.

EXAMPLE 1

A multilayer color photographic light-sensitive material was prepared by coating the layers as described hereinafter on a cellulose triacetate film support.

Layer 1: Antihalation Layer

To 1 kg of a black colloidal silver emulsion (containing 15 g of blackened silver and 100 g of gelatin per 1 kg of the emulsion) was added 40 ml of a 5% by weight aqueous solution of a coating agent, sodium p-dodecylbenzenesulfonate, and the resultant mixture was coated on the support in a dry film thickness of 2μ.

Layer 2: Gelatin Intermediate Layer (dry film thickness: 1.0μ)

Layer 3: Red-Sensitive, Low-Sensitive Silver Halide Emulsion Layer

A silver iodobromide emulsion (mean grain size: 0.3μ; containing 100 g of silver halide and 70 g of gelatin per 1 kg of the emulsion) containing 5 mol% of iodine was prepared in the usual manner. To 1 kg of the emulsion thus prepared were added 210 ml of a 0.1% by weight methanol solution of anhydro-5,5-dichloro-9-ethyl-3,3'-di(3-sulfopropyl)thiacarbocyaninehydroxide pyridinium salt as a red-sensitive spectral sensitizer, and then 20 ml of a 5% by weight aqueous solution of 5-methyl-7-hydroxy-2,3,4-triazaindolizine, 400 g of Cyan Coupler Emulsion (1) and 200 g of Emulsion (2), both being as described hereinafter. Then, 200 ml of a 2% by weight aqueous solution of Colored Cyan Coupler (CC-1) was added to the mixture as prepared above, and additionally, 30 ml of a 2% by weight aqueous solution of a 2-hydroxy-4,6-dichlorotriazine sodium salt as a gelatin hardener was added thereto to prepare a red-sensitive, low-sensitive silver halide emulsion. This emulsion was coated in a dry film thickness of 3.5μ.

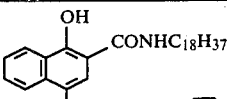

Emulsion (1)

| | |
|---|---|
| Sodium p-dodecylbenzenesulfonate | 5 g |
| Tricresyl phosphate | 60 ml |
| Cyan Coupler (C-101) | 70 g |
| Ethyl acetate | 100 ml |

These compounds were mixed and dissolved at 55° C. The resultant mixture was added to 1,000 g of a 10% by weight aqueous solution of gelatin which had been previously heated to 55° C., and emulsified in a colloid mill.

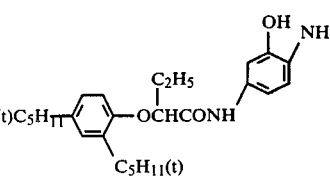

Emulsion (2)

| | |
|---|---|
| Sodium p-dodecylbenzenesulfonate | 5 g |
| Tricresyl phosphate | 60 ml |
| Cyan Coupler (C-101) | 70 g |
| DIR Compound (D-1) | 10 g |
| Ethyl acetate | 100 ml |

These compounds were mixed and dissolved at 55° C. The resultant mixture was added to 1,000 g of a 10% by weight aqueous solution of gelatin which had been previously heated to 55° C., and emulsified in a colloid mill.

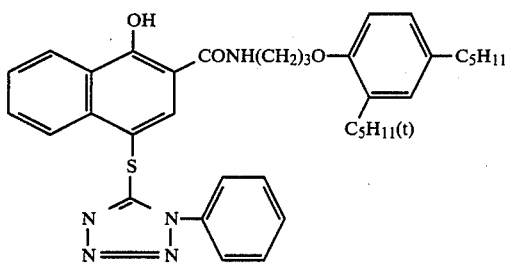

D-1

Layer 4: Red-Sensitive, High-Sensitive Silver Halide Emulsion Layer

A silver halide solution was prepared in the same manner as in the preparation of Layer 3 except that the following changes were made:

| Mean grain size of emulsion | 0.9 μ |
| --- | --- |
| Amount of red-sensitive color sensitizer added | 140 ml |
| Emulsion (1) | 220 g |
| Emulsion (2) | 30 g |

The solution thus prepared was coated in a dry film thickness of 2.2μ.

Layer 5: Gelatin Intermediate Layer (dry film thickness: 0.8μ)

Layer 6: Green-Sensitive, Low-Sensitive Silver Halide Emulsion Layer

To 1 kg of the same silver iodobromide emulsion as used in the preparation of Layer 3, 180 ml of a 0.1% methanol solution of a 3,3'-di(2-sulfoethyl)-9-ethylbenzoxacarbocyanine pyridinium salt as a green-sensitive sensitizing dye and 20 ml of a 5% by weight aqueous solution of 5-methyl-7-hydroxy-2,3,4-triazaindolizine were added successively. Then, 320 g of Magenta Coupler Emulsion (3) and Emulsion (4), both being as described hereinafter, were added thereto. In addition, 50 ml of a 2% by weight aqueous solution of 2-hydroxy-4,6-dichlorotriazine sodium salt as a gelatin hardener was added to prepare a green-sensitive, low-sensitive silver halide emulsion. The emulsion thus prepared was coated in a dry film thickness of 3.2μ.

Layer 7: Green-Sensitive, High-Sensitive Silver Halide Emulsion Layer

A silver halide solution was prepared in the same manner as in the preparation of Layer 6 except that the following changes were made:

| Mean grain size of emulsion | 1.0 μ |
| --- | --- |
| Iodine content of emulsion | 6.5 mol % |
| Amount of green-sensitive color sensitizer added | 100 ml |
| Emulsion (3) | 150 g |
| Emulsion (4) | 30 g |

The silver halide solution thus prepared was coated in a dry film thickness of 2.2μ.

| Emulsion (3) | |
| --- | --- |
| Sodium p-dodecylbenzenesulfonate | 5 g |
| Tricresyl phosphate | 80 ml |
| Magenta Coupler (M-101) | 50 g |
| Colored Magenta Coupler (CM-1) | 10 g |
| Ethyl acetate | 120 ml |

These compounds were mixed and dissolved at 55° C. The resultant mixture was added to 1,000 g of a 10% by weight aqueous solution of gelatin which had been previously heated to 55° C., and emulsified in a colloid mill.

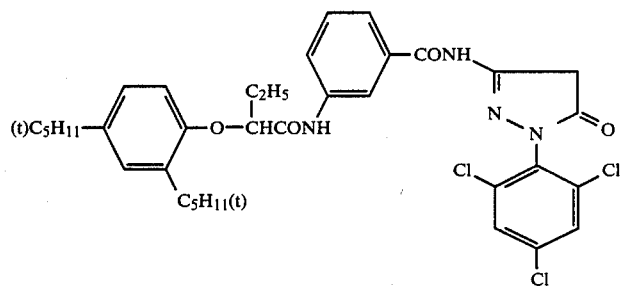

M-101

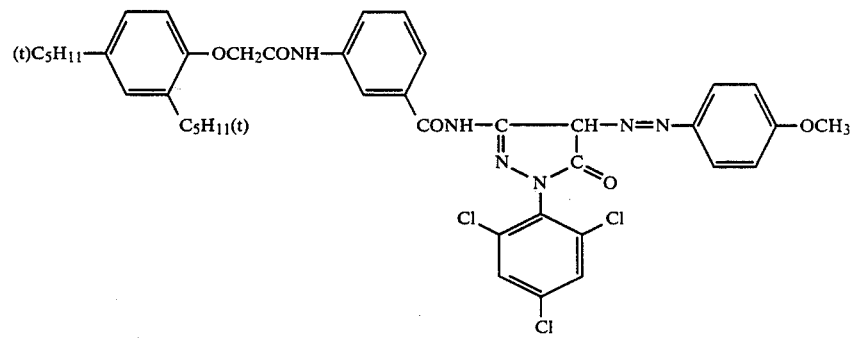

CM-1

| Emulsion (4) | |
| --- | --- |
| Sodium p-dodecylbenzenesulfonate | 5 g |
| Tricresyl phosphate | 80 ml |

| | |
|---|---|
| Magenta Coupler (M-101) | 50 g |
| Colored Magenta Coupler (CM-1) | 10 g |
| DIR Compound (D-2) | 15 g |
| Ethyl acetate | 120 ml |

These compounds were mixed and dissolved at 55° C. The resultant mixture was added to 1,000 g of a 10% by weight aqueous solution of gelatin which had been previously heated to 55° C., and emulsified in a colloid mill.

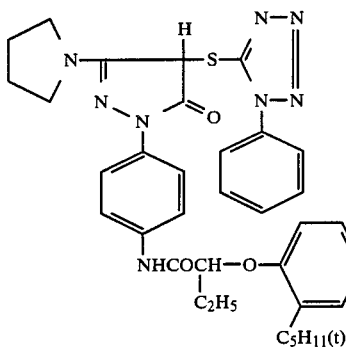

D-2

| Emulsion (5) | |
|---|---|
| Yellow Coupler (Y-1) | 100 g |
| Ethyl acetate | 120 ml |

These compounds were mixed and dissolved at 55° C. The resultant mixture was added to 1,000 g of a 10% by weight aqueous solution of gelatin which had been previously heated to 55° C., and emulsified in a colloid mill.

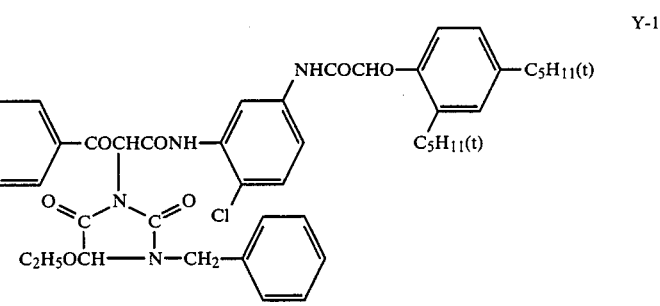

Y-1

Layer 8: Yellow Filter Layer

To 1 kg of a yellow colloidal silver emulsion (containing 8.9 g of yellow colloidal silver and 67 g of gelatin per 1 kg of the emulsion) was added 100 ml of a 5% by weight aqueous solution of sodium p-dodecylbenzene sulfonate as a coating agent. The resultant mixture was coated in a dry film thickness of 1.6μ. The amount of silver coated was 50 mg/m².

Layer 9: Blue-Sensitive, Low-Sensitive Silver Halide Emulsion Layer

To 1 kg of the same silver iodobromide emulsion as used in the preparation of Layer 3 except that the mean grain size was 0.5μ were added 20 ml of a 5% by weight aqueous solution of 5-methyl-7-hydroxy-2,3,4-triazaindolizine and 1,500 g of Yellow Coupler Emulsion (5) as described hereinafter. Additionally, 50 ml of a 2% by weight aqueous solution of 2-hydroxy-4,6-dichlorotriazine sodium salt as a gelatin hardener was added to prepare a blue-sensitive, low-sensitive silver halide emulsion.

The emulsion thus prepared was coated in a dry film thickness of 3.0μ.

| Emulsion (5) | |
|---|---|
| Sodium p-dodecylbenzenesulfonate | 5 g |
| Tricresyl phosphate | 80 ml |

Layer 10: Blue-Sensitive, High-Sensitive Silver Halide Emulsion Layer

A silver halide solution was prepared in the same manner as in the preparation of Layer 9 except that the following changes were made:

| | |
|---|---|
| Mean grain size of emulsion | 1.1 μ |
| Emulsion (5) | 300 g |

The solution thus prepared was coated in a dry film thickness of 2.5μ.

Layer 11: Gelatin Protective Layer (dry film thickness: 1.5μ)

The thus-prepared light-sensitive material is designated as "Film 1".

To the yellow filter layer of Film 1 were added 1-phenyl-5-mercaptotetrazole and the compounds of the invention (in the form of a methanol solution) as shown in Table 1 each in an amount of $2.1 \times 10^{-2}$ mol per mol of silver to prepare the corresponding light-sensitive materials. These light-sensitive materials are designated, respectively, as Films 2 to 17.

Films 1 to 17 as prepared above were subjected to the force storage testing under the conditions as described below so that changes naturally occurring over a long period of time could be observed in a short period of time.

Storage Conditions for the Forced Storage Testing

Condition (1): Stored at room temperature for 3 days.

Condition (2): Stored at 50° C. and 60% RH for 3 days.

Condition (3): Stored at 45° C. and 80% RH for 3 days.

Then, each light-sensitive material was exposed wedgewise to light and developed as described hereinafter. The characteristic curve of the green-sensitive layer adjacent to the yellow filter layer was obtained by the automatic density measurement. Based on the characteristic curve, the minimum density, $D_{min}$, and relative logarithmic sensitivity, $S_{0.2}$ (determined by the exposure amount providing a density of fog+0.2) of the green-sensitive layer was determined. The results are shown in Table 1.

| Processing Step | Temperature (°C.) | Time |
|---|---|---|
| Color development | 41 | 3 min. |
| Stopping | 38 | 30 sec. |
| Washing | " | 30 sec. |
| Bleach-accelerating bath | " | 30 sec. |
| Bleaching | " | 3 min. |
| Washing | " | 1 min. |
| Fixing | " | 2 min. |
| Washing | " | 2 min. |
| Stabilizing bath | " | 10 sec. |

The processing solutions used had the following compositions.

| Color Developer | | |
|---|---|---|
| Sodium hydroxide | 2 | g |
| Sodium sulfite | 2 | g |
| Potassium bromide | 1.4 | g |
| Sodium chloride | 1 | g |
| Borax | 1 | g |
| Hydroxylamine sulfuric acid salt | 4 | g |
| Disodium ethylenediaminetetraacetate | 2 | g |
| 4-Amino-3-methyl-N—ethyl-N—(β-hydroxyethyl)aniline monosulfate | 4 | g |
| Water to make | 1,000 | ml |
| Stopping Solution | | |
| Water | 800 | ml |
| Glacial acetic acid | 30.0 | ml |
| Caustic soda | 1.65 | g |
| Water to make | 1,000 | ml |
| Bleach-Accelerating Solution | | |
| Sodium sulfite (anhydrous) | 9.0 | g |
| 2-N,N—Dimethylaminoethylisothiourea dihydrochloride | 2.5 | g |
| Sodium acetate | 8.0 | g |
| Glacial acetic acid | 2.3 | ml |
| Water to make | 1,000 | ml |
| Bleaching Solution | | |
| Sodium persulfate | 60 | g |
| Sodium chloride | 20 | g |
| Sodium dihydrogenphosphate | 15 | g |
| Sodium tetrapolyphosphate | 2 | g |
| β-Alanine | 2 | g |
| Phosphoric acid (85%) | 2.2 | ml |
| Water to make | 1,000 | ml |
| Fixing Solution | | |
| Sodium thiosulfate | 150 | g |
| Sodium sulfite (anhydrous) | 15 | g |
| Borax | 12 | g |
| Glacial acetic acid | 15 | ml |
| Water to make | 1,000 | ml |
| Stabilizing Solution | | |
| Formaldehyde (37%) | 10 | ml |

In order to examine the desilvering speed of the yellow colloidal silver of Films 1 to 17, the minimum yellow color density was measured when the bleaching as described above was performed for 1 minute as well as for 3 minutes. As the difference in density between the bleaching time of 1 minute and that of 3 minutes is great, the amount of yellow colloidal silver remaining near the center of the light-sensitive material after the processing is large. The results are shown in Table 2.

TABLE 1

Results of Forced Storage Testings

| Film No. | Type of Antifoggant | Green-Sensitive Layer $D_{min}$ Storage Condition | | | Green-Sensitive Layer $S_{0.2}$ Storage Condition | | |
|---|---|---|---|---|---|---|---|
| | | 1 | 2 | 3 | 1 | 2 | 3 |
| 1 | — | 0.57 | 0.56 | 0.65 | −2.09 | −2.11 | −1.92 |
| 2 | 1-Phenyl-5-mercaptotetrazole | 0.52 | 0.52 | 0.58 | −2.11 | −2.12 | −1.90 |
| 3 | Compound (1) | 0.52 | 0.51 | 0.54 | −2.12 | −2.12 | −1.99 |
| 4 | Compound (3) | 0.52 | 0.50 | 0.54 | −2.12 | −2.14 | −1.99 |
| 5 | Compound (5) | 0.52 | 0.51 | 0.53 | −2.13 | −2.13 | −2.00 |
| 6 | Compound (7) | 0.52 | 0.52 | 0.54 | −2.12 | −2.12 | −1.97 |
| 7 | Compound (8) | 0.52 | 0.52 | 0.54 | −2.11 | −2.12 | −1.97 |
| 8 | Compound (10) | 0.52 | 0.50 | 0.54 | −2.12 | −2.14 | −1.99 |
| 9 | Compound (12) | 0.52 | 0.51 | 0.54 | −2.11 | −2.12 | −1.98 |
| 10 | Compound (14) | 0.52 | 0.51 | 0.53 | −2.11 | −2.11 | −1.97 |
| 11 | Compound (16) | 0.52 | 0.51 | 0.54 | −2.11 | −2.12 | −1.98 |
| 12 | Compound (18) | 0.53 | 0.52 | 0.55 | −2.11 | −2.12 | −1.97 |
| 13 | Compound (19) | 0.53 | 0.52 | 0.55 | −2.11 | −2.12 | −1.97 |
| 14 | Compound (21) | 0.53 | 0.53 | 0.56 | −2.10 | −2.10 | −1.96 |
| 15 | Compound (23) | 0.52 | 0.52 | 0.54 | −2.12 | −2.12 | −1.98 |
| 16 | Compound (25) | 0.52 | 0.51 | 0.53 | −2.13 | −2.13 | −2.00 |
| 17 | Compound (27) | 0.52 | 0.51 | 0.53 | −2.12 | −2.12 | −1.99 |

TABLE 2

| Film No. | Type of Antifoggant | Minimum Yellow Color Density | |
|---|---|---|---|
| | | Bleached for 1 Minute | Bleached for 3 Minutes |
| 1 | — | 1.16 | 1.15 |
| 2 | 1-Phenyl-5-mercaptotetrazole | 1.16 | 1.10 |
| 3 | Compound (1) | 1.11 | 1.10 |
| 4 | Compound (3) | 1.11 | 1.10 |
| 5 | Compound (5) | 1.11 | 1.10 |
| 6 | Compound (7) | 1.12 | 1.10 |
| 7 | Compound (8) | 1.11 | 1.10 |
| 8 | Compound (10) | 1.11 | 1.10 |
| 9 | Compound (12) | 1.11 | 1.10 |
| 10 | Compound (14) | 1.12 | 1.10 |
| 11 | Compound (16) | 1.11 | 1.10 |
| 12 | Compound (18) | 1.12 | 1.10 |
| 13 | Compound (19) | 1.12 | 1.10 |
| 14 | Compound (21) | 1.13 | 1.10 |
| 15 | Compound (23) | 1.12 | 1.10 |
| 16 | Compound (25) | 1.12 | 1.10 |
| 17 | Compound (27) | 1.12 | 1.10 |

As apparent from Table 1 or 2, the use of the compounds of the invention makes it possible to inhibit an increase in fog of the adjacent layer due to the presence of colloidal silver and, moreover, to decrease the range of variation in sensitivity. Particularly under the storage condition (3) (wet conditions), the compounds of the invention exhibit a marked fog preventing effect. Thus, by using the antifoggants of the invention, the fog change occurring when the light-sensitive material is stored for a long period of time can be reduced and a desirable photograph having a reduced variation in photographic sensitivity can be obtained.

Of compounds exhibiting a fog-preventing action, 1-amidophenyl-5-mercaptotetrazole, for example, forms a stable silver salt, deteriorating desilvering properties. Hence, in the case of bleaching using persulfates, for example, having a low bleaching force, the amount of such a compound being used should be inevitably minimized because of its desilvering-inhibiting properties. As apparent from Table 2, when 1-phenyl-5-mercaptotetrazole is used in an effective amount to prevent fog, the yellow density is high because of poor desilvering, whereas the compounds of the invention exhibit almost no desilvering-preventing properties (poor desilvering of yellow colloidal silver). In the case of Films 3 to 17 in which the compounds of the invention were added, even if the bleaching time was shortened, the amount of remaining black colloidal silver was smaller than that of Film 2 in which 1-phenyl-5-mercaptotetrazole was added and was nearly equal to that of the control, Film 1.

EXAMPLE 2

On a cellulose triacetate film provided with the usual subbing layer were coated successively the three layers as described below to prepare a light-sensitive material.

Layer 1: Silver Halide Emulsion Layer

A silver iodobromide emulsion (mean grain size: $1.2\mu$; containing 100 g of silver halide and 70 g of gelatin per 1 kg of the emulsion) containing 6.5 mol% of iodine was prepared in the usual manner. To 1 kg of the emulsion thus prepared were added 20 ml of a 5% by weight aqueous solution of 5-methyl-7-hydroxy-2,3,4-triazaindolizine and 500 g of a magenta coupler emulsion as described hereinafter, and additionally, 30 ml of a 2% by weight aqueous solution of 2-hydroxy-4,6-dichlorotriazine sodium salt to prepare a silver halide emulsion. The emulsion thus prepared was coated in a dry film thickness of $5.0\mu$.

| Emulsion (1) | |
|---|---|
| Sodium p-dodecylbenzenesulfonate | 5 g |
| Tricresyl phosphate | 80 ml |
| Magenta Coupler (M-101 as used in Example 1) | 50 g |
| Ethyl acetate | 100 ml |

These compounds were mixed and dissolved at 55° C. The resultant mixture was added to 1,000 g of a 10% by weight aqueous solution of gelatin which had been previously heated to 55° C., and emulsified in a colloid mill.

Layer 2: Gelatin Protective Layer (dry film thickness: $1.5\mu$)

The light-sensitive material as prepared above is designated as "Film 20".

To the silver halide emulsion layer of Film 20 was added each of 1-phenyl-5-mercaptotetrazole and the compounds of the invention as shown in Table 3 in an amount of $0.3 \times 10^{-4}$ or $1 \times 10^{-4}$ mol per mol of silver halide. In the case of the compounds of the invention, they were added in the form of a methanol solution. The thus prepared light-sensitive materials are designated as "Films 21 to 46".

Films 20 to 46 were each subjected to the same forced storage testing as in Example 1.

Storage Conditions for Forced Storage Testings

Condition (1): Stored at room temperature for 3 days.

Condition (2): Stored at 50° C. and 60% RH for 3 days.

Condition (3): Stored at 45° C. and 80% RH for 3 days.

Each light-sensitive material was exposed wedgewise to light and developed as described hereinafter. The magenta color density was measured by means of an automatic densitometer. Based on the magenta color density, the fog density and the relative logarithmic sensitivity, $S_{0.2}$ (as determined by the exposure amount providing a density of fog+0.2), were determined. The results are shown in Table 3.

The processing conditions were as follows:

| Processino Step | Time | Temperature (°C.) |
|---|---|---|
| Color development | 3 min. 15 sec. | 38 |
| Bleaching | 6 min. 30 sec. | " |
| Washing | 3 min. 15 sec. | " |
| Fixing | 6 min. 30 sec. | " |
| Washing | 3 min. 15 sec. | " |
| Stabilizing | 3 min. 15 sec. | " |

The composition of the processing solution at each step was as follows:

| Color Developer | |
|---|---|
| Sodium nitrilotriacetate | 1.0 g |
| Sodium sulfite | 4.0 g |
| Sodium carbonate | 30.0 g |
| Potassium bromide | 1.4 g |
| Hydroxylamine sulfuric acid salt | 2.4 g |
| 4-(N—Ethyl-N—β-hydroxyethylamino)-2-methylaniline sulfuric acid salt | 4.5 g |
| Water to make | 1,000 ml |
| Bleaching Solution | |
| Ammonium bromide | 160.0 ml |
| Ammonia water (28%) | 25.0 ml |
| Sodium iron ethylenediaminetetraacetate | 130 g |
| Glacial acetic acid | 14 ml |
| Water to make | 1,000 ml |
| Fixing Solution | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1,000 ml |
| Stabilizing Solution | |
| Formalin | 8.0 ml |
| Water to make | 1,000 ml |

TABLE 3

| | | | Results of Forced Storage Testings | | | | | |
|---|---|---|---|---|---|---|---|---|
| | | Amount | Fog Density | | | $S_{0.2}$ | | |
| Film | Type of | (mol/silver) | Storage Condition | | | Storage Condition | | |
| No. | Antifoggant | halide mol) | 1 | 2 | 3 | 1 | 2 | 3 |
| 20 | — | 0 | 0.32 | 0.31 | 0.42 | −2.23 | −2.17 | −1.50 |
| 21 | 1-Phenyl-5-mercaptotetrazole | $0.3 \times 10^{-4}$ | 0.29 | 0.27 | 0.39 | −2.26 | −2.21 | −1.65 |
| 22 | 1-Phenyl-5-mercaptotetrazole | $1.0 \times 10^{-4}$ | 0.26 | 0.25 | 0.38 | −2.30 | −2.24 | −1.70 |
| 23 | Compound (1) | $0.3 \times 10^{-4}$ | 0.26 | 0.24 | 0.35 | −2.29 | −2.26 | −1.78 |
| 24 | " | $1.0 \times 10^{-4}$ | 0.22 | 0.21 | 0.28 | −2.38 | −2.32 | −1.84 |
| 25 | Compound (3) | $0.3 \times 10^{-4}$ | 0.26 | 0.25 | 0.35 | −2.29 | −2.27 | −1.78 |
| 26 | " | $1.0 \times 10^{-4}$ | 0.22 | 0.22 | 0.28 | −2.38 | −2.31 | −1.84 |
| 27 | Compound (9) | $0.3 \times 10^{-4}$ | 0.27 | 0.27 | 0.36 | −2.28 | −2.25 | −1.73 |
| 28 | " | $1.0 \times 10^{-4}$ | 0.23 | 0.22 | 0.30 | −2.34 | −2.30 | −1.80 |
| 29 | Compound (10) | $0.3 \times 10^{-4}$ | 0.26 | 0.24 | 0.35 | −2.29 | −2.26 | −1.78 |
| 30 | " | $1.0 \times 10^{-4}$ | 0.23 | 0.22 | 0.28 | −2.37 | −2.30 | −1.83 |
| 31 | Compound (13) | $0.3 \times 10^{-4}$ | 0.26 | 0.24 | 0.35 | −2.29 | −2.26 | −1.77 |
| 32 | " | $1.0 \times 10^{-4}$ | 0.23 | 0.22 | 0.28 | −2.37 | −2.31 | −1.82 |
| 33 | Compound (15) | $0.3 \times 10^{-4}$ | 0.26 | 0.25 | 0.35 | −2.28 | −2.24 | −1.73 |
| 34 | " | $1.0 \times 10^{-4}$ | 0.23 | 0.23 | 0.31 | −2.34 | −2.29 | −1.80 |
| 35 | Compound (17) | $0.3 \times 10^{-4}$ | 0.27 | 0.26 | 0.36 | −2.29 | −2.25 | −1.73 |
| 36 | " | $1.0 \times 10^{-4}$ | 0.23 | 0.22 | 0.31 | −2.34 | −2.30 | −1.81 |
| 37 | Compound (20) | $0.3 \times 10^{-4}$ | 0.27 | 0.26 | 0.36 | −2.29 | −2.24 | −1.72 |
| 38 | " | $1.0 \times 10^{-4}$ | 0.23 | 0.22 | 0.30 | −2.34 | −2.29 | −1.79 |
| 39 | Compound (22) | $0.3 \times 10^{-4}$ | 0.26 | 0.24 | 0.35 | −2.28 | −2.25 | −1.73 |
| 40 | " | $1.0 \times 10^{-4}$ | 0.23 | 0.22 | 0.29 | −2.37 | −2.30 | −1.80 |
| 41 | Compound (23) | $0.3 \times 10^{-4}$ | 0.27 | 0.27 | 0.35 | −2.28 | −2.24 | −1.74 |
| 42 | " | $1.0 \times 10^{-4}$ | 0.23 | 0.22 | 0.30 | −2.35 | −2.30 | −1.80 |
| 43 | Compound (25) | $0.3 \times 10^{-4}$ | 0.27 | 0.27 | 0.34 | −2.28 | −2.24 | −1.75 |
| 44 | " | $1.0 \times 10^{-4}$ | 0.23 | 0.22 | 0.29 | −2.35 | −2.30 | −1.81 |
| 45 | Compound (28) | $0.3 \times 10^{-4}$ | 0.27 | 0.27 | 0.35 | −2.28 | −2.25 | −1.76 |
| 46 | " | $1.0 \times 10^{-4}$ | 0.23 | | 0.30 | −2.35 | −2.30 | −1.82 |

As apparent from Table 3, the use of the compounds of the invention makes it possible to prevent the formation of fog in the emulsion layer as in the case of the incorporation in the colloidal silver layer and to obtain a great increase in sensitivity. Moreover, the range of variation in sensitivity with time is small. In particular, the fog-preventing effect under the condition (3) (wet conditions) is remarkable. Thus, even by using the antifoggants of the invention in the emulsion layer, very good photographic performance can be obtained.

While the invention has been described in detail and with reference to specific embodiments thereof, it will be apparent to one skilled in the art that various changes and modifications can be made therein without departing from the spirit and scope thereof.

What is claimed is:

1. A photographic silver halide light-sensitive material containing at least one of the compounds represented by general formula (I) as described below, their salts, and their precursors releasing the compounds of general formula (I) on cleavage under alkali conditions

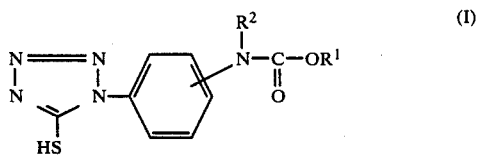

wherein $R^1$ is a substituted or unsubstituted aliphatic group, or a substituted or unsubstituted aromatic group, and $R^2$ is a hydrogen atom, a substituted or unsubstituted aliphatic group, or a substituted or unsubstituted aromatic group; $R^1$ and $R^2$ are the same or are different and can combine together to form a ring.

2. A photographic silver halide light-sensitive material as claimed in claim 1, wherein $R^1$ and $R^2$ represent an alkyl group or an alkenyl group containing 1 to 18 carbon atoms.

3. A photographic silver halide light-sensitive material as claimed in claim 1, wherein $R^1$ and $R^2$ represent an aryl group containing 6 to 20 carbon atoms.

4. A photographic silver halide light-sensitive material as claimed in claim 1, wherein $R^1$ is a phenyl group or an alkyl group containing 1 to 8 carbon atoms.

5. A photographic silver halide light-sensitive material as claimed in claim 1, wherein $R^2$ is a hydrogen atom, an alkyl group containing 1 to 6 carbon atoms or a phenyl group.

6. A photographic silver halide light-sensitive material as claimed in claim 1, wherein the compound selected from the group consisting of compounds represented by general formula (I), salts and precursors thereof, is present in a silver halide emulsion layer in an amount in the range of $10^{-8}$ to $10^{-2}$ mol per mol of silver halide.

7. A photographic silver halide light-sensitive material as claimed in claim 1, wherein the compound selected from the group consisting of compounds represented by general formula (I), salts and precursors thereof, is present in a silver halide emulsion layer in an amount in the range of $10^{-6}$ to $10^{-3}$ mol per mol of silver halide.

8. A photographic silver halide light-sensitive material as claimed in claim 1, wherein the compound selected from the group consisting of compounds represented by general formula (I), salts and precursors thereof, is present in a colloidal silver-containing layer in an amount in the range of $10^{-4}$ to 1 mol per mol of silver.

9. A photographic silver halide light-sensitive material as claimed in claim 1, wherein the compound selected from the group consisting of compounds represented by general formula (I), salts and precursors thereof, is present in a colloidal silver-containing layer in an amount in the range of $10^{-3}$ to $10^{-1}$ mol per mol of silver.

10. A photographic silver halide light-sensitive material as claimed in claim 8, wherein the colloidal silver-containing layer is an antihalation layer or a yellow filter layer.

11. A photographic silver halide light-sensitive material as claimed in claim 1, wherein $R^1$ is an unsubstituted aliphatic group, or a substituted or unsubstituted aromatic group.

* * * * *